US00PP35474P2

(12) United States Plant Patent
Bergman

(10) Patent No.: US PP35,474 P2
(45) Date of Patent: Nov. 14, 2023

(54) ***CHRYSANTHEMUM* PLANT NAMED 'CIDZ0114'**

(50) Latin Name: ***Chrysanthemum* x *morifolium***
Varietal Denomination: CIDZ0114

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/971,693

(22) Filed: Oct. 24, 2022

(51) Int. Cl.
*A01H 5/02* (2018.01)
*A01H 6/14* (2018.01)

(52) U.S. Cl.
USPC ..... Plt./295

(58) Field of Classification Search
USPC ..... Plt./295, 284, 286
CPC ..... A01H 5/1424
See application file for complete search history.

*Primary Examiner* — Susan McCormick Ewoldt
(74) *Attorney, Agent, or Firm* — Dale Skalla

(57) ABSTRACT

A new *Chrysanthemum* plant named 'CIDZ0114' particularly distinguished by its yellow-gold daisy-type inflorescences, excellent flower production, vigorous growth and spreading plant habit, and very uniform flowering with response time of 7.5 weeks when grown under short days.

1 Drawing Sheet

Latin name of the genus and species of the plant claimed: *Chrysanthemum* x *morifolium.*

Varietal denomination: 'CIDZ0114'.

BACKGROUND OF THE NEW PLANT

The present invention comprises a new *Chrysanthemum*, botanically known as *Chrysanthemum* x *morifolium*, and hereinafter referred to by the variety name 'CIDZ0114'.

'CIDZ0114' is a product of a planned breeding program. The new cultivar has yellow-gold daisy-type inflorescences, excellent flower production, vigorous growth and spreading plant habit, and very uniform flowering with response time of 7.5 weeks when grown under short days.

'CIDZ0114' originates as a natural whole plant mutation discovered among flowering plants of 'CIDZ0101' commercially known as 'Flagstaff Topaz', growing in a greenhouse in Gilroy, Calif. in July 2018.

The parent is the proprietary plant 'CIDZ0101', U.S. Plant Pat. No. 33,144, having inflorescences of a butterscotch bronze hue under usual conditions, while it is similar to 'CIDZ0114' in most all other characteristics.

The first act of asexual reproduction of 'CIDZ0114' was accomplished when vegetative stem cuttings were propagated from the initial selection in October 2018 in a greenhouse in Gilroy, Calif.

BRIEF SUMMARY OF INVENTION

Horticultural examination of plants grown from cuttings of the plant, initiated October 2018, and continuing thereafter, has demonstrated that the combination of characteristics as herein disclosed for 'CIDZ0114' are firmly fixed and are retained through successive generations of asexual reproduction.

'CIDZ0114' has not been observed under all possible environmental conditions. The phenotype may vary significantly with variations in environment such as temperature, light intensity and day length.

A Plant Breeder's Right for this cultivar was applied for in Canada on Oct. 21, 2022, No. 22-11110. 'CIDZ0114' has not been made publicly available prior to the effective filing date of this application, notwithstanding any disclosure that may have been made less than one year prior to the effective filing date of this application by the inventor or another who obtained 'CIDZ0114' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0114' with colors being as true as possible with an illustration of this type.

Figure 1:
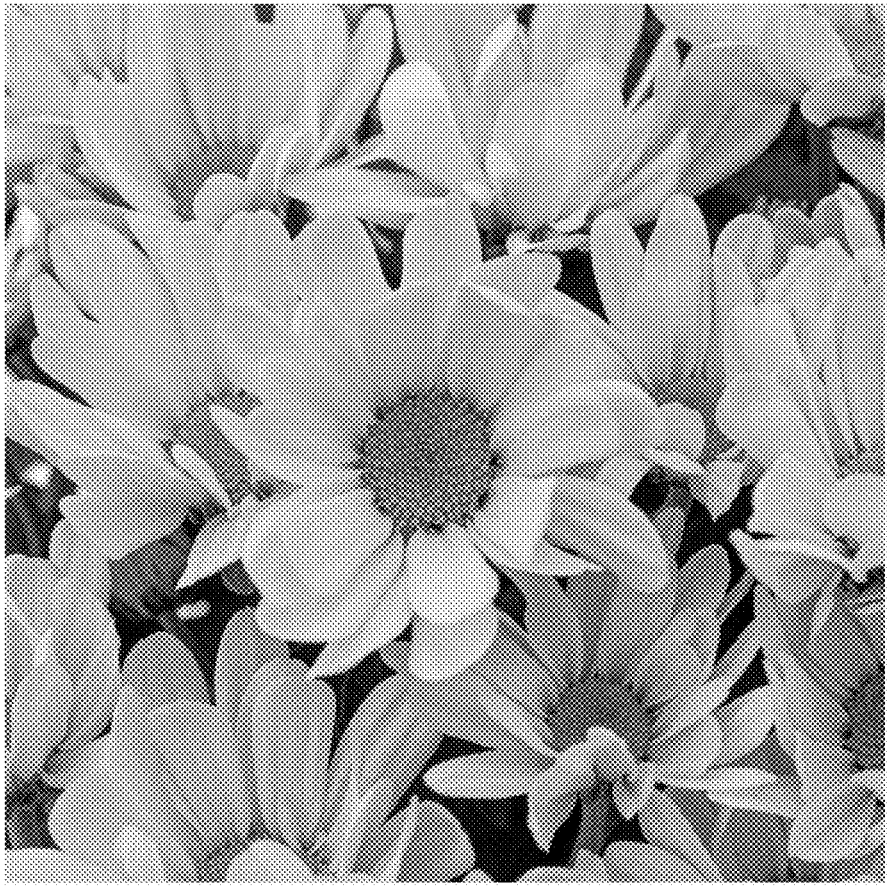
Figure 2:
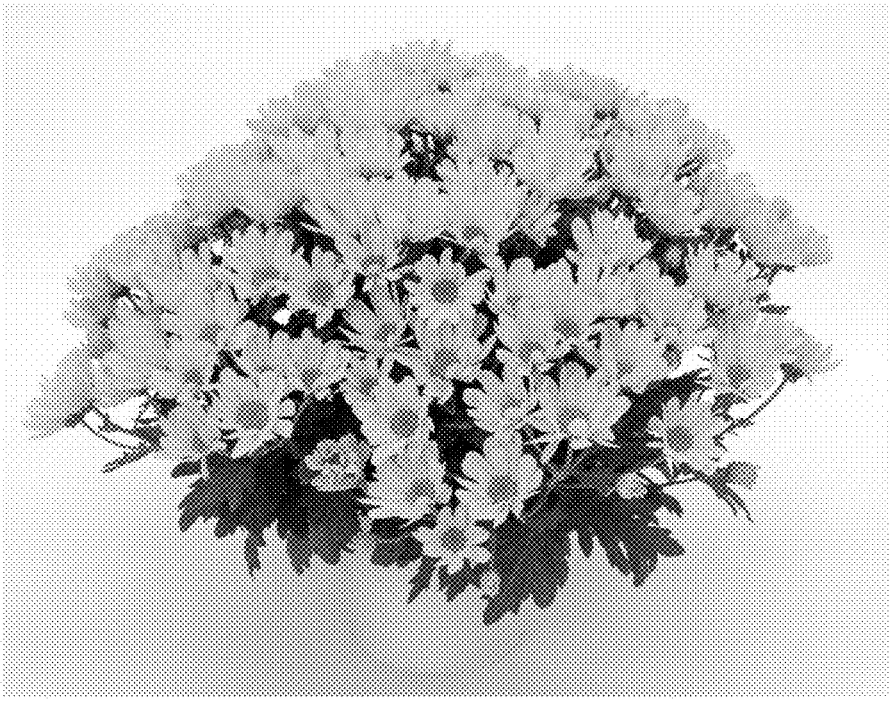

The photographic drawings show in FIG. 1 a close-up view of the inflorescense of the new variety and in FIG. 2 a whole flowering plant grown in a greenhouse.

DETAILED BOTANICAL DESCRIPTION

The plant descriptions and measurements were taken indoors in Gilroy, Calif. in August 2022 on about 11 week old plants. Unrooted cuttings had been planted, 4 plants per pot, in 6 inch pots in May 2022. The plants were pinched and moved to short days in June 2022 to induce flowering.

The aforementioned photographs: FIGS. 1 and 2 was taken in Gilroy, Calif. in May 2022, and showing a plant from a trial, in which flowering had been induced by applying black cloth.

These plants were about 11 weeks of age. Unrooted cuttings had been planted, 4 plants per pot, in 6 inch pots. The plants were pinched and moved to short days to induce flowering.

Color references are made to The Royal Horticultural Society Colour Chart (RHS) 2001.

TABLE 1

DIFFERENCES BETWEEN THE NEW VARIETY 'CIDZ0114' AND A MOST SIMILAR VARIETY:

| | 'CIDZ0114' | 'Yochesapeake', U.S. Plant Pat. No. 12,535 |
|---|---|---|
| Flower quantity: | More | Fewer |
| Flowering response: | One week faster | One week slower |
| Flower size: | Smaller | Larger |

Plant:

*Form, growth and habit.*—Herbaceous pot-type, stems upright, freely branching, strong and moderately vigorous growth habit.

*Plant height.*—26.0 cm.

*Plant height (inflorescence included).*—30.0 cm.

*Plant width.*—46.0-48.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137C.

*Lower surface.*—RHS 138A.

*Mature, leaf color, upper surface.*—RHS 137A.

*Lower surface.*—RHS 138A.

*Length.*—7.2-7.9 cm.

*Width.*—4.8-5.8 cm.

*Shape.*—Ovate.

*Base shape.*—Attenuate.

*Apex shape.*—Acute.

*Margin.*—Palmately lobed; irregularly incised, somewhat serrate.

*Texture, upper surface.*—Bifid T-shaped hairs.

*Lower surface.*—Bifid T-shaped hairs.

*Color of veins, upper surface.*—Closest to RHS 138D.

*Color of veins, lower surface.*—RHS 147D.

*Pattern of veining.*—Palmate.

*Petiole color.*—RHS 138A.

*Length.*—2.0-3.1 cm.

*Diameter.*—0.3-0.5 cm.

*Texture.*—Bifid T-shaped hairs.

Stem:

*Quantity of main branches per plant.*—5-6.

*Color of stem.*—RHS 138B.

*Length of stem.*—15-18 cm.

*Diameter.*—0.4-0.6 cm.

*Length of internodes.*—0.6-1.3 cm.

*Texture.*—Bifid T-shaped hairs.

*Color of peduncle.*—RHS 138B.

*Length of peduncle.*—6.5-13.0 cm.

*Peduncle diameter.*—0.25-0.35 cm.

*Texture.*—Bifid T-shaped hairs.

*Stipule color.*—RHS 137A.

*Stipule length.*—0.6-0.9 cm.

*Stipule width.*—0.3-0.6 cm.

Inflorescence:

*Type.*—Compositae type, solitary daisy-type inflorescences borne terminally above foliage, ray florets arranged acropetally on a capitulum.

*Quantity of short days to flowering (response time).*—7.5 weeks.

*Natural season flowering.*—Not determined for this variety.

*Quantity of inflorescences per plant.*—Average of 38.

*Lastingness of individual blooms on the plant.*—4 weeks.

*Fragrance.*—Slightly spicy.

Bud (just when opening/showing color):

*Color.*—RHS 3C.

*Length.*—1.1 cm.

*Width.*—1.2 cm.

*Shape.*—Oblate.

Immature inflorescence:

*Diameter.*—4.6 cm.

*Color of ray florets, upper surface.*—RHS 5A.

*Lower surface.*—RHS 5B.

Mature inflorescence:

*Diameter.*—6.7-7.2 cm.

*Depth.*—3.0-3.4 cm.

*Total diameter of disc.*—1.7-1.8 cm.

*Receptacle color.*—RHS 145A.

*Receptacle height.*—0.3 cm.

*Receptacle diameter.*—0.6 cm.

Ray florets:

*Average quantity of florets.*—22.

*Color of ray florets, upper surface.*—RHS 5A.

*Lower surface.*—RHS 5B.

*Length.*—2.9-3.2 cm.

*Width.*—1.1-1.2 cm.

*Shape.*—Eliptical.

*Shape at longitudinal axis.*—Straight.

*Apex shape.*—Rounded to emarginate.

*Margin.*—Entire.

*Length of corolla tube.*—Short.

*Texture, upper surface.*—Papillose.

*Lower surface.*—Papillose.

Disc florets:

*Average quantity of florets.*—220.

*Color of florets.*—RHS 151C apex, RHS 8B mid portion basally fading to RHS 1D.

*Length.*—0.5-0.6 cm.

*Width.*—0.15-0.25 cm when open.

*Shape.*—Tubular, elongated.

*Apex shape.*—Acute, 5 pointed.

Phyllaries:

*Quantity.*—average of 30.

*Color, upper surface.*—RHS 137A.

*Lower surface.*—RHS 137A.

*Length.*—0.7-0.9 cm.

*Width.*—1.5-0.2 cm.

*Shape.*—Lanceolate.

*Apex shape.*—Acute.

*Base.*—Fused.

*Margins.*—Entire; slightly papery.

*Texture, upper surface.*—Glabrous.

*Lower surface.*—Bifid T-shaped hairs.

Reproductive organs:

*Pistil.*—1, found on both types of florets.

*Length.*—0.6 cm.

*Style color.*—RHS 145D.

*Style length.*—0.5 cm.

*Stigma color.*—RHS 12A.

*Stigma shape.*—Bi-parted.

*Ovary color.*—RHS 155C but more translucent.

*Stamens.*—4, found on only on the disc florets.
*Color of filaments.*—RHS 155C.
*Length filaments.*—0.4-0.5 cm.
*Anther color.*—RHS 13A.
*Anther length.*—0.15 cm.
*Anther shape.*—Oval.
*Color of pollen.*—RHS 13A.
*Pollen amount.*—Sparse.
*Fertility/seed set.*—Has not been observed to date.
*Disease/pest resistance.*—Has not been observed to date.
*Plant hardiness.*—Has not been observed to date.

What is claimed is:

1. A new and distinct variety of *Chrysanthemum* plant named 'CIDZ0114' substantially as illustrated and described herein.

* * * * *